United States Patent [19]

Inman et al.

[11] Patent Number: 5,837,255
[45] Date of Patent: Nov. 17, 1998

[54] METHOD OF REDUCING BLOOD GLUCOSE BY ADMINISTERING HARUNGANIN OR VISMIN

[75] Inventors: Wayne DeWald Inman, Belmont; Jian Luo, Brisbane, both of Calif.

[73] Assignee: Shaman Pharmaceuticals, Inc., South San Francisco, Calif.

[21] Appl. No.: 762,785

[22] Filed: Dec. 10, 1996

[51] Int. Cl.$^6$ .......................... A61K 35/78; A61K 38/28; A61K 31/12; C07C 50/18
[52] U.S. Cl. .............................. 424/195.1; 514/3; 514/4; 514/323; 514/369; 514/635; 514/680; 514/884; 552/271
[58] Field of Search ..................... 514/766, 680, 514/3, 4, 21, 53, 323, 635, 369, 884; 552/271; 424/195.1

[56] References Cited

PUBLICATIONS

Abbiw, 1990, *Useful Plants of Ghana* (Intermediate Technology Publications Ltd., London).
Cepleanu et al., 1994, "Screening of tropical medicinal plants for Molluscicidal, larvicidal, Fungicidal and Cytotoxic Activities and Brine Shrimp Toxicity", Int. J. Pharmacog. 32:294–307.
Chapuis et al., 1988, "Screening for Cytotoxic Activity of Plants Used in Traditional Medicine", J. Ethnopharmacol. 23:273–284.
Delle Monache et al., "Chemistry of Vismia Genus. Note V: γ–Hydroxy–and γ,γ'–Dihydroxy–Ferruginin A", J. Nat. Prod. 43:487–494.
Delle Monache et al., 1979, "Ferruginin A and B and Ferruanthrone, New Triprenylated Anthranoids from *Vismia baccifera* Var. Ferruginea", Tetrahedron 35:2143–2149.
Dell Monache et al., 1979, "Vismiones from *Vismia baccifera* Var. Dealdata (H.B.K.): Chemistry and X–Ray Structure Determination", Gazzetta Chimica Italiana 109:301–310.
Della Monache et al. 1980, "Chemistry of Gene Vismia" Planta Medica 40:340–346.
Gessler et al., 1994, "Screening Tanzanian Medicinal Plants for Antimalarial Activity", Acta Tropica 56:65–77.
Gessler et al., 1995, "Tanzanian Medicinal Plants Used Traditionally for the Treatment of Malaria: In Vivo Antimalarial and In Vitro Cytotoxic Activities", Phytotherapy Res. 9;504–508.
Haerdi, 1964, "Native Medical Plants of Ulanga District of Tanganyika (East Africa)" Dissertation, Verlag Fur Recht und Gessellschaft AG, Basel, Switzerland.
Hakizamungu et al., 1992, "Screening of Rwandese Medicinal Plants for Anti–Trichomonas Activity", J. Ethnopharmacol. 36:143–146.

Iwu, 1993, *Handbook of African Medicinal Plants* (CRC Press, Boca Raton).
MacFoy and Sama, 1983, "Medicinal Plants in Pujehun District of Sierra Leone", J. Ethnopharmacol. 8:215–223.
Madubunyi et al., 1995, "Antihepatotoxic and Antimicrobial Activites of *Harungana Madagascariensis* Leaf Extracts", Int. J. Pharmacol. 33:129–134.
Maikere–Faniyo et al., 1989, "Study of Rwandese Medicinal Plants Used in the Treatment of Diarrhoea I", J. Ethnopharmacol. 26:101–109.
Nagem and Ferreira, 1993, "Compositions of *Vismia micrantha*", Fitoterapia 64:382–383.
Neuwinger, 1996, *African Ethnobotany: Poisons and Drugs* (Chapman & Hall, New York).
Nicoletti and Marini–Bettolo, 1982, "Keto–Enolic Tautomerism and Spectral Data of Prenylated Anthranoids from Vismia Genus", Tetrahedron 38:3679–3686.
Nwodo, 1989, "Antibiotic and Anti–inflammatory Analgesic Activities of *Harungana madagascariensis* Stem Bark", Int. J. Crude Drug Res. 27:137–140.
Ritchie and Taylor, 1964, "The Constituents of *Harungana Madagascariensis* Poir.", Tetrahedron Lett. 23:1431–1436.
Sandberg and Cronlund, 1977, "What Can We Still Learn from Traditional Folklore Medicine?", Proc. Third Asian Symposium, Medicinal Plants and Spices, Colombo, Sri Lanka, Feb. 2–6.
Schultes and Raffauf, 1990, *The Healing Forest* (Dioscorides Press, Portland) pp. 210–212.
Schultes, 1983, "Biodynamic Guttiferous Plants of the Northwest Amazon", Bot. Mus. Leaflets 29:49–57.
Stout et al., 1962, "Harunganin: A Crystallographic Determination of an Unknown Structure", J. Am. Chem. Soc. 84:2653–2654.
Franke et al., Therapie Der Gegenwart, 105:266–269, 1966.
Remington's Pharmaceutical Sciences, 16th Ed., Mack Publishing Co., Easton, PA, pp. 202–208, 1980.
The Merck Index, 10th Ed., Merck & Co., Inc., Rahway, NJ, p. 204, Entry #1445, and pp. 849–850, Entry #5792, 1983.
The Merck Manual Of Diagnosis And Therapy, vol. 1, General Medicine, 15th Ed., Merck & Co., Inc., Rahway, NJ, pp. 759, 1343, 822–835, 1987.

*Primary Examiner*—David M. Naff
*Assistant Examiner*—Janet M. Kerr
*Attorney, Agent, or Firm*—Pennie & Edmonds LLP

[57] ABSTRACT

The use of extracts from Harungana or Vismia spp. or anthracenone compounds harunganin and vismin contained therein or isolated therefrom as hypoglycemic agents, as well as methods for obtaining the hypoglycemic agents are described. According to a preferred embodiment, the extracts are derived from *H. madagascariensis*. As hypoglycemic agents, the extracts or anthracenone compounds harunganin and vismin are useful for treating insulin-dependent (type I) and non-insulin-dependent (type II) diabetes.

14 Claims, 6 Drawing Sheets

METHOD OF REDUCING BLOOD GLUCOSE BY ADMINISTERING HARUNGANIN OR VISMIN

TABLE OF CONTENTS
1. FIELD OF THE INVENTION
2. BACKGROUND OF THE INVENTION
   2.1 Medicinal Uses of Harungana
   2.2 Medicinal Uses of Vismia
   2.3 Isolation of Harunganin and Vismin
3. SUMMARY OF THE INVENTION
4. DESCRIPTION OF THE FIGURES
5. DETAILED DESCRIPTION OF THE INVENTION
   5.1 Process for Preparing Hypoglycemically Active Extracts and/or Compounds
   5.2 Methods for Using Extracts of Harungana or Vismia Spp
   5.3 Methods for Use of Harunganin and Vismin
6. EXAMPLE: PREPARATION OF AN AQUEOUS DECOCTION FROM *H. MADAGASCARIENSIS*
7. EXAMPLE: ISOLATION AND CHARACTERIZATION OF HARUNGANIN AND VISMIN
   7.1 Materials and Methods
   7.2 Isolation of Harunganin and Vismin Using Solvent Extraction
   7.3 Structure Elucidation of Harunganin and Vismin
      7.3.1 Spectroscopic Properties of Harunganin
      7.3.2 Spectroscopic Properties of Vismin
8. EXAMPLE: REDUCTION OF PLASMA GLUCOSE
   8.1 Materials and Methods
   8.2 Results
9. EXAMPLE: TIME COURSE EFFECT ON PLASMA GLUCOSE
   9.1 Materials and Methods
   9.2 Results
10. EXAMPLE: EFFECT ON GLUCOSE DISPOSAL
    10.1 Materials and Methods
    10.2 Results
11. EXAMPLE: EFFECTS ON GLUCOSE TRANSPORT IN 3T3-L1 ADIPOCYTES
    11.1 Materials and Methods
    11.2 Results

1. FIELD OF THE INVENTION

This invention pertains to the use of extracts from Harungana spp. or Vismia spp. (family Guttiferae), including, but not limited to *H. madagascariensis* or *Vismia macrophylla*, as well as harunganin and vismin anthracenone compounds, for the treatment of diabetes mellitus; methods for isolation of hypoglycemic extracts and purification of hypoglycemic compounds; and compositions comprising and methods for the use of harunganin and vismin.

2. BACKGROUND OF THE INVENTION

2.1 Medicinal Uses of Harungana

*Harungana madagascariensis* (Lam. ex. Poir) is a small to medium-sized tree that grows commonly throughout many parts of west, central, and east Africa. The leaves, bark, and roots are used medicinally in rural and urban areas of a variety of African countries.

The Igbo, Efik, and Doko-uyanga cultures in southeast Nigeria use this plant medicinally in the following ways: leaves are mixed with water, made into a paste and applied topically to treat ringworm, varicella, conjunctivitis, rashes and fevers; fresh leaf juice is applied topically to treat abscesses; young leaves are boiled in water and the resulting "tea" is administered orally three times a day as an analgesic and to treat whooping cough. In addition, a dried leaf infusion is administered orally in Nigeria to treat jaundice, stomach problems and leprosy, and is used as an oxytocic and abortifacient (I. I. Madubunyi et al., *Int. J. Pharmacog.* 332:129–134 (1995); P. A. Akah, *Phytotherapy Res.* 8:106–108 (1994)). Furthermore, a bark decoction is used in Nigeria to treat asthma, stomach ulcers, liver problems, and as a purgative.

In East Africa, a hot water extract of *H. madagascariensis* bark is administered orally to treat malaria and to interrupt menses (J. Kokwaro, *Medicinal Plants of East Africa*, East Africa Literature Bureau, Nairobi, (1976)).

In Guinea, a hot water extraction of the bark is administered orally to facilitate child delivery and expulsion of the placenta, and treat painful menstruation (B. Vasileva, *Plantes Medicinales de Guinee*, Conakry, Republique de Guinee (1969)). The Fang of Equatorial Guinea administer bark extract orally to treat liver disorders and fever, and use an extract as an enema to treat inflammation.

In Rwanda, a dried stem bark decoction is administered orally to treat malaria (E. Hakizamungu et al., *J. Ethnopharmacol.* 362:143–146 (1992)) and diarrhea (R. Ma ïkere-Faniyo et al.,*J. Ethnopharmacol.* 26:101–109 (1989)). In addition, the stem bark and leaf extract is administered to treat urogenital infections, malaria, and diarrhea.

In Tanzania, malaria is treated by administering an oral extract of a dried root, stem bark and leaf decoction (M. C. Gessler et al., *Acta Tropica* 56:65–77 (1994)), or a dried stem bark infusion (M. C. Gessler et al., *Phytother. Res.* 9:504–508 (1995)).

A hot water extract of the entire plant is used in the Ivory Coast as an aphrodisiac and emmenagogue (A. Bouquet et al., *Trav. Doc. Orstom.* 32:1 (1974)).

In Sierra Leone, a hot water extraction of the fruit is administered orally as an abortive (B. Vasileva, *Plantes Medicinales de Guinee*, Conakry, Republique de Guinee (1969)). In addition, plant juice is applied to treat scabies and other skin diseases, leaf powder is used to treat ulcers, and leaf extract is administered orally to treat asthma.

In Tanganyika, leaf juice is administered orally to treat amenorrhea (F. Haerdi, *Native Medicinal Plants of Ulanga District of Tanganyika* (East Africa), Dissertation, Verlag F ür Recht und Gesellschaft AG, Basel, Switzerland (1964)).

D. K. Abbiw, in *Useful Plants of Ghana*, Intermediate Technology Publications & The Royal Botanic Gardens, Kew (1990), reports the following uses for this plant: bark extract is used to treat River Blindness, mange and toothache, as an anthelminthic and as a child's purgative; fresh roots and buds are used to treat stomachache; bark decoction is used to treat asthma, hepatitis, ulcers and dysmenorrhoea, and to induce vomiting; leaves are used to treat chest complaints and pains; root is used to treat diarrhea and dysentery; gummy sap is administered as an enema to treat enteritis and is used to treat leprosy, ringworm, skin diseases, and affections (parasitic); berries and young shoots and buds are used to treat gastro-intestinal pains or disorders; bark infusion and root is used to treat jaundice; crushed bark is used to hasten expulsion of the placenta; bark is used to treat scurvy; stems are used to treat stomach pain, disorders, and indigestion; sap is used to arrest bleeding; young shoots are used to treat gonorrhea; and the plant's latex is used as an arrow poison.

M. Iwu, in *Handbook of African Medicinal Plants*, CRC Press, Boca Raton, Fla. (1993), reports that the leaves, roots and stems of *H. madagascariensis* are used to treat acute stomachache, toothaches, dysentery, and hemorrhoids.

H. D. Neuwinger, in *African Ethnobotany: Poisons and Drugs*, Chapman & Hall, London (1996), reports the following medicinal uses of *H. madagascariensis:* the Manon culture of Liberia administer bark decoction orally to treat tapeworms, mix buds in palm oil and orally administer the resulting mixture to treat maternity patients and puerperal fever, and apply shoot juice to stop bleeding from circumcision;

the Wemenu healers of Benin use a root extract to treat urinary tract infections;

peoples from the southeast Tanzania section of Ulanga administer bark powder orally to treat malaria, and administer root bark powder orally to treat hookworms;

in Cameroon, the Bafia women administer bark decoction orally after giving birth, the Bamileke boil young leaves in oil and salt and administer the mixture orally after miscarriage, and the Fang culture administer crushed leaf soup to treat people who are believed to be bewitched;

in Gabon, the tree sap or stem bark decoction is applied to circumcision wounds, and used as a cicatrizant;

the Pygmies of the Lobaye river in southwest Central African Republic administer a stem bark decoction orally, and use a plant extract as a bath to treat diarrhea and dysentery;

in the Bangui region of the Central African Republic, a bark decoction is used to treat menstrual troubles and blennorrhagia, bark powder is applied to wounds, leaf decoction is administered to treat stomachache, yellow inner bark sap is applied topically over the abdomen of women for treatment of infertility, root is used as an antidote against vegetal poisons;

in Zaire, the Kote culture macerate bark and bathe with it to treat scabies, and bark and root decoctions are administered to treat bleeding hemorrhoids and dysentery, and the Turumba culture treat anemia by bathing in a leaf infusion dripping leaf juice onto the eye. The Mbuti pygmy culture from the Lolwa river in the Ituri forest of Northeast Zaire utilize the bark for abdominal problems, skin rash, and eczema;

in the Ouessa region of the Congo, the bark macerate is administered orally to treat hematuria and jaundice, root bark decoction is administered orally, used as a hip bath, or administered vaginally to treat infertility, dysmenorrhea, and repeated miscarriage; bark decoction is administered orally to treat cough and bronchial affections, and used as an expectorant; and the leaf sap is used to treat heart problems;

in Burundi, leaf decoction is used as a bath or as an inhalant to treat epilepsy, leaf decoction used to treat vaginal prolapse, leaf decoction is administered orally to treat coughs and tapeworms, root decoction is used to treat tapeworms; and in Madagascar, leaf tea is taken for diarrhea, flatulence, gastrointestinal problems, septic sore throat, tuberculosis, and fever; plant juice is used to treat scabies, and plant parts are administered orally after rich meals to regulate digestion.

Studies of various extracts from Harungana plant parts have shown antibiotic and anti-inflammatory activities, (O. F. C. Nwodo, *Int. J. Crude Drug Res.* 27:137–140 (1989)); anti-hepatotoxic and antimicrobial activities (I. I. Madubuny, et al., *Int. J. Pharmacog.* 33:129–134 (1995)); and molluscicidal activity and cytotoxicity (F. Cepleanu et al., *Int. J. Phamacog.* 32:294–307 (1994) and J. C. Chapuis et al., *J. Ethnophamacol.* 33:273–284 (1988)).

The bark extract of *H. madagascariensis* has also been screened for pharmacological activities by a single intraperitoneal injection in rats. The bark extract caused death in 5 hours and had a minimal lethal dose of 500 mg/kg, and failed to show any of the pharmacological effects screened for including; motor activity, muscle relaxation, analgesia, pilomotor erection, eno exophthalmus, ptosis, pupil size, ear coloration, micturition, diarrhea, or lacrimation (F. Sandburg and A. Cronlund, *Proc. Third Asian Symposium, Medicinal Plants and Spices*, Colombo, Sri Lanka, Feb. 2–6, (1977)).

2.2 Medicinal Uses of Vismia

*Vismia* spp. are trees or tall shrubs growing primarily in the tropical and subtropical regions of South and Central America, but a few species are also found in Africa and Asia (F. Delle Monache et al., *Planta Medica* 40:340–346 (1980) ). Of the roughly fifty *Vismia* spp. known, fifteen are found in Venezuela (F. Delle Monache, *Gazzeta Chimica Italiana* 109:301 (1979)).

The latex from *Vismia angusta* is used throughout the Colombian Amazonia to treat wounds and infected sores, and is used by the Tikunas to treat skin fungus and herpes of the lips; a tea from *Vismia confertiflora* is used by the Yukunas and Makunas of the Ríos Miritiparaná and Popeyaka, possibly as a diuretic; the orange "latex" from *Vismia dealbata* is used by the Puinaves to treat skin maladies believed to be of fungal origin; the resin of *Vismia ferruginea* in applied to wounds in Amazonian Brazil, Peru and Colombia; a decoction of leaves from *Vismia guineensis*, together with leaves from *Canthium glabriflorum*, is used as a blood tonic for children in the Pujehun District of Sierra Leone, West africa; *Vismia micrantha* has been used as a purgative, tonic, febrifuge and an anti-rheumatic; and an exudate of *Vismia tomentosa* is used by the Makunas to treat red skin rashes (C. A. MacFoy et al., *Journal of Ethnopharmacology* 8:215–23 (1983); R. E. Schultes, Botanical Museum Leaflets, 29(1):49–57 (1983); R. E. Schultes et al., "The Healing Forest: Medicinal and Toxic Plants of the Northwest Amazonia," Vol. 2, pp. 210–12 , T. R. Dudley, ed., Dioscorides Press, Portland, Oreg. (1990); T. J. Nagem et al., *Fitoterapia* 64(4):382–83 (1993)).

In the Ivory Coast, Vismia is used to treat fever and skin disorders (A. Bouquet et al., *Trav. Doc. Orstom.* 32:1 (1984)).

Studies of stem bark extracts from Vismia spp. have shown molluscicidal and fungicidal activity (F. Cepleanu et al., *Int. J. Pharmacog.* 32:294–307 (1994)) and cytotoxic activity (J. C. Chapuis et al., *J. Ethnopharmacol.* 23:273–284 (1988)).

2.3 Isolation of Harunganin and Vismin

Harunganin was isolated previously from *H. madagascariensis*, and its structure was determined by X-ray analysis (G. H. Stout et al., *J. Am. Chem. Soc.* 84:2653 (1962); E. Ritche et al., *Tetrahedron Lett.* 1431 (1964)). Some of harunganin's spectroscopic properties have been reported (F. Delle Monache et al., *Tetrahedron* 35:2143–2149 (1979); F. Delle Monache et al., *J. Nat. Prod.* 43(4):487–494 (1980); M. Nicoletti et al., *Tetrahedron* 38:3679 (1982)).

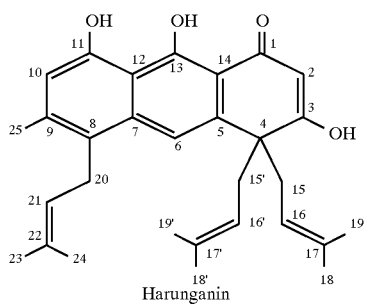

Harunganin

Vismin was isolated from *Vismia macrophylla* (F. Delle Monache et al., *Planta Med.* 40:340 (1980)). Some of vismin's spectroscopic properties have been reported (Nicoletti et al., *Tetrahedron* 38:3679 (1982); F. Delle Monache et al., *Planta Med.* 40:340 (1980)).

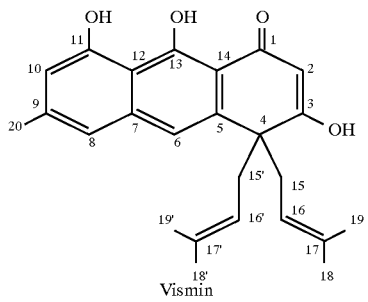

Vismin

To the knowledge of the inventors, no prior study has described any hypoglycemic activity of extracts of Harungana spp. or Vismia spp., nor was there any prior suggestion that anthracenone compounds such as harunganin or vismin are useful as hypoglycemic agents.

Citation or identification of any reference in Section 2 of this application shall not be construed as an admission that such reference is available as prior art to the present invention.

3. SUMMARY OF THE INVENTION

The present invention provides a method for the use of extracts from Harungana spp. or from Vismia spp., and for the use of anthracenone compounds harunganin and vismin, as well as pharmaceutically acceptable salts thereof, as hypoglycemic agents or as agents to lower blood glucose levels, particularly in diabetic subjects.

One embodiment of the invention encompasses extracts of Harungana or Vismia spp. and methods for using the extracts, (or anthracenone compounds harunganin or vismin contained therein or a pharmaceutically acceptable salt thereof), for the treatment of insulin-dependent diabetes mellitus or non-insulin dependent diabetes mellitus in mammals, including humans. Also encompassed are methods for using the hypoglycemic agents to reduce blood glucose in mammals, including humans, in situations of acute stress.

Another embodiment of the invention encompasses a method for using harunganin or vismin, or a pharmaceutically acceptable salt thereof, as a hypoglycemic agent.

The invention also encompasses a method for using harunganin or vismin, or a pharmaceutically acceptable salt thereof, as a blood glucose lowering agent in diabetic subjects. The invention also encompasses pharmaceutical compositions for use as a hypoglycemic agent in mammals, comprising a therapeutically effective amount of harunganin or vismin, or a pharmaceutically acceptable salt thereof and a pharmaceutical carrier, as well as methods for using such pharmaceutical compositions.

According to an embodiment of the invention, a therapeutically effective hypoglycemic agent is prepared by a method comprising the steps of:
(a) washing plant material from an Harungana or a Vismia sp. with a first polar or non-polar solvent to obtain a solution of one or more hypoglycemically active compounds;
(b) concentrating the solution to obtain an enriched mixture containing said one or more hypoglycemically active compounds; and
(c) performing at least one iteration of the steps:
    (i) partitioning the enriched mixture containing said one or more hypoglycemically active compounds in a biphasic mixture of a second polar solvent and a second non-polar solvent to obtain a bioactive non-polar solution, wherein said second polar solvent is immiscible in said second non-polar solvent; and
    (ii) concentrating said bioactive non-polar solution.

According to a another embodiment of the invention, a method for reducing blood glucose in a mammal comprises administering, to a mammal in need of such blood glucose reduction, a therapeutically effective amount of an extract from Harungana or Vismia spp., said extract obtained by a process comprising the steps of:
(a) washing plant material from an Harungana or a Vismia sp. with a first polar or non-polar solvent to obtain a solution of one or more hypoglycemically active compounds;
(b) concentrating the solution to obtain an enriched mixture containing said one or more hypoglycemically active compounds; and
(c) performing at least one iteration of the steps:
    (i) partitioning the enriched mixture containing said one or more hypoglycemically active compounds in a biphasic mixture of a second polar solvent and a second non-polar solvent to obtain a bioactive non-polar solution, wherein said second polar solvent is immiscible in said second non-polar solvent; and
    (ii) concentrating said bioactive non-polar solution to obtain extract useful as a hypoglycemic agent.

Still further, the invention encompasses methods for treatment of diabetes mellitus comprising administering, to a mammal suffering from diabetes mellitus, a therapeutically effective amount of an extract from Harungana or Vismia spp. in which said extract was obtained by a process which comprised:
(a) washing plant material from an Harungana or a Vismia sp. with a first polar or non-polar solvent to obtain a solution of one or more hypoglycemically active compounds;
(b) concentrating the solution to obtain an enriched mixture containing said one or more hypoglycemically active compounds; and
(c) performing at least one iteration of the steps:
    (i) partitioning the enriched mixture containing said one or more hypoglycemically active compounds in a biphasic mixture of a second polar solvent and a second non-polar solvent to obtain a bioactive non-polar solution, wherein said second polar solvent is immiscible in said second non-polar solvent; and
    (ii) concentrating said bioactive non-polar solution.

Further still, the invention includes pharmaceutical compositions for use as hypoglycemic agents in mammals, comprising a therapeutically effective amount of an extract from Harungana or Vismia spp., in which said extract was obtained by a process which comprised:

(a) washing plant material from an Harungana or Vismia sp. with a first polar or non-polar solvent to obtain a solution of one or more hypoglycemically active compounds;

(b) concentrating the solution to obtain an enriched mixture containing said one or more hypoglycemically active compounds; and (c) performing at least one iteration of the steps:
  (i) partitioning the enriched mixture containing said one or more hypoglycemically active compounds in a biphasic mixture of a second polar solvent and a second non-polar solvent to obtain a bioactive non-polar solution, wherein said second polar solvent is immiscible in said second non-polar solvent; and
  (ii) concentrating said bioactive non-polar solution.

The present invention may be understood more fully by reference to the following figures, detailed description and illustrative examples which are intended to exemplify non-limiting embodiments of the invention.

4. DESCRIPTION OF THE FIGURES

FIG. 1 is a bar graph showing the plasma glucose levels (mg/dl) of diabetic mice treated with harunganin. Harunganin was administered at 5 mg/kg (q.d., 2 doses) and 50 mg/kg (q.d., single dose). All data points N=8. $P<0.01$; *$P<0.001$ (analysis of variance (ANOVA), one factor). See Section 8.2 for details.

FIG. 2 is a graph showing time course of the reduction of plasma glucose levels (mg/dl) of diabetic mice treated with harunganin. Animals received the relevant compound (or vehicle) at 100 mg/kg (q.d., single dose). All data points N=8. **$P<0.001$ (analysis of variance (ANOVA), one factor). See Section 9.2 for details.

FIG. 3 is a graph showing the reduction of post-prandial plasma glucose levels with harunganin in the oral glucose tolerance test. Animals received the relevant compound, orally, daily for 3 days at 5, 25 and 50 mg/kg followed by a glucose bolus on day 3. All data points N=8. *$P<0.05$; $P<0.01$; *$P<0.001$ (analysis of variance (ANOVA), one factor). See Section 10 for details.

FIG. 4 is a bar graph showing the reduction of the area under the curve with administration of harunganin in the oral glucose tolerance test. Animals received harunganin, orally, daily for 3 days at 5, 25 and 50 mg/kg. All data points N=8. *$P<0.05$; $P<0.01$; *$P<0.001$ (analysis of variance (ANOVA), one factor). See Section 10.2 for details.

5. DETAILED DESCRIPTION OF THE INVENTION

Figure 1:
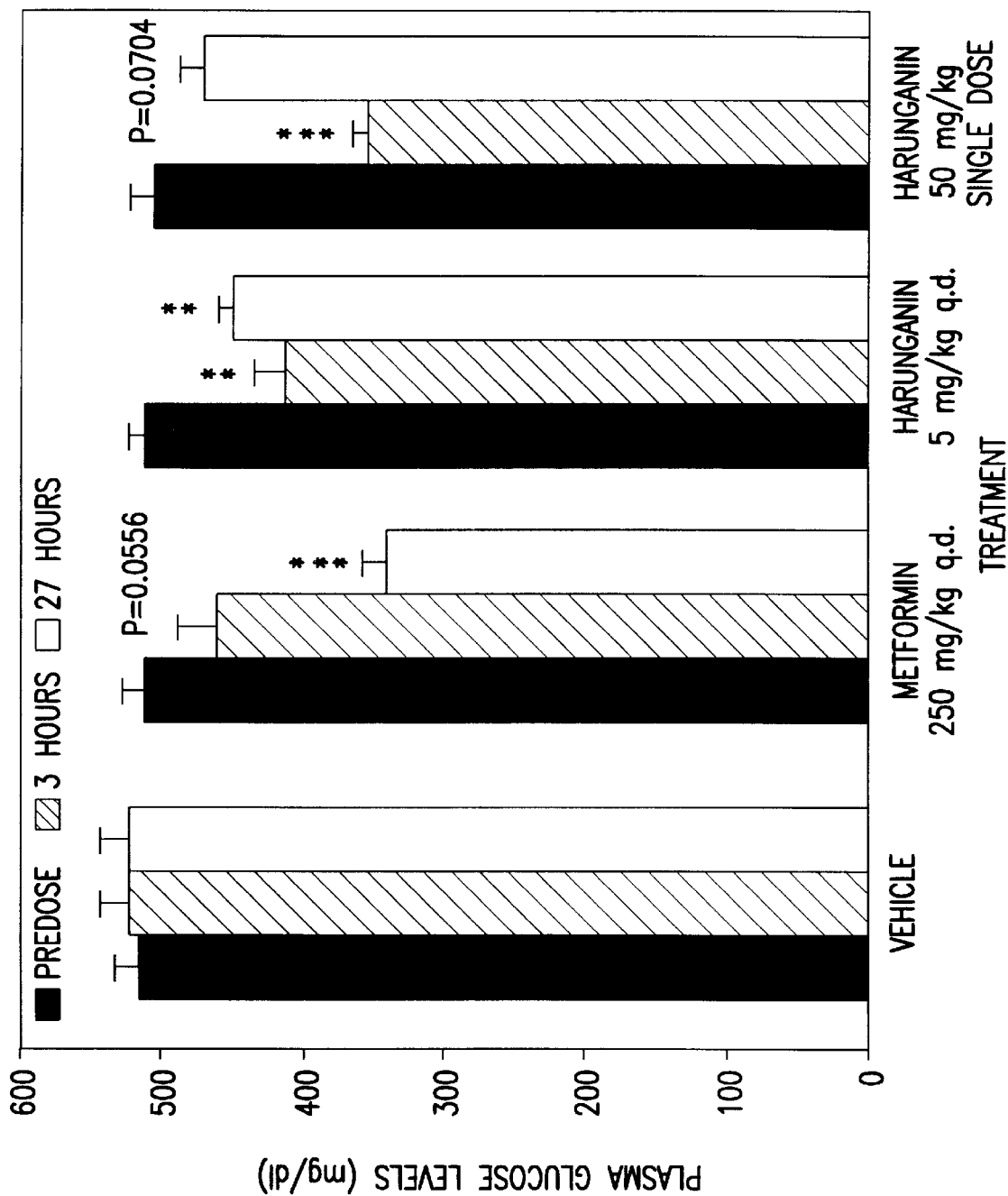

5.1 Process for Preparing Hypoglycemically Active Extracts and/or Compounds

The anthracenone compounds harunganin and vismin employed in the methods and pharmaceutical compositions of the present invention can be isolated from Harungana spp. or Vismia spp., preferably from *H. madagascariensis*, either as components of hypoglycemically active extracts, or in substantially purified form, using the illustrative methods described below.

According to the present invention, a hypoglycemic extract can be prepared from an Harungana sp. or a Vismia sp., preferably from *H. madagascariensis*, according to the methods described below.

Whole plant material from an Harungana sp. or a Vismia sp., preferably from *H. madagascariensis*, is washed with a first polar or non-polar solvent to obtain a solution of one or more hypoglycemically active compounds. Preferably, the plant material is taken from the leaf and stem bark. Suitable first polar solvents include, but are not limited to, methanol, ethanol, 2-methoxyethanol, 1-propanol, 2-propanol, iso-butanol, sec-butanol, tetrahydrofuran, other polar solvents know to those skilled in the art, and mixtures thereof. The first polar solvent may optionally be diluted with water in order to adjust the polarity thereof. In this case, the aqueous content of the first polar solvent can range from 0 to about 50%, preferably from 0 to about 20%.

Suitable first non-polar solvents include, but are not limited to, diethyl ether, ethyl acetate, isoamyl acetate, benzene, toluene, xylene, 2-butanone, 4-methyl-2-pentanone, chlorinated hydrocarbons such as dichloromethane, chloroform, carbon tetrachloride, 1,2-dichloroethane, tetrachloroethylene, and other non-polar solvents known to those skilled in the art, and mixtures thereof.

Preferably, the first polar or non-polar solvent used to wash plant material from an Harungana sp. or a Vismia sp. is a polar solvent, more preferably, ethanol, and most preferably, about 8:2 ethanol/water.

It is to be understood that prior to washing with the first polar or non-polar solvent, plant material can optionally be ground, for example in a Wiley mill, or otherwise reduced in overall size, so as to increase the effective surface area of the plant material available to the solvent.

The washing of plant material can be facilitated by placing it in a suitable vessel with first polar or non-polar solvent, and allowing the mixture to stir for about 30 minutes to about two weeks, preferably for about 3 hours to about 72 hours, and most preferably from about 12 hours to about 48 hours. The first polar or non-polar solvent can be at room temperature, or heated at a temperature from about room temperature to about the reflux temperature for the particular solvent system employed. optionally, plant material from an Harungana or a Vismia sp. can be extracted using a Soxhlet extraction apparatus and the first polar or non-polar solvent by methods known to those skilled in the art.

The resulting solution containing one or more hypoglycemically active compounds is concentrated, optionally in vacuo, to provide an enriched mixture containing one or more hypoglycemically active compounds. The solution of one or more hypoglycemically active compounds can optionally be filtered through, e.g., conventional filter paper, celite, or a small layer of silica gel, prior to concentration.

The resulting enriched mixture containing one or more hypoglycemically active compounds is subjected to at least one iteration of the steps of (i) partitioning the enriched mixture in a biphasic mixture of a second polar solvent and a second non-polar solvent to obtain a bioactive non-polar solution and (ii) concentrating the bioactive non-polar solution to obtain an extract concentrate comprising harunganin or vismin, and useful as a hypoglycemic agent. These steps can be performed as many times as necessary to extract one or more hypoglycemically active compounds, e.g., harunganin or vismin, from the enriched mixture and into the second non-polar solvent, such that the resulting extract concentrate contains the one or more hypoglycemically active compounds. In a preferred embodiment, one of the one or more hypoglycemically active compounds is harunganin or vismin. Preferably the number of iterations of steps (i) and (ii) can range from one to six, most preferably, two. Suitable second polar solvents include, but are not limited to, water and aqueous solutions of the following solvents: methanol, ethanol, 1-propanol, 2-propanol, iso-butanol, sec-butanol, tetrahydrofuran, other polar solvents known to those skilled in the art, and mixtures thereof. Suitable second non-polar solvents include, but are not limited to those first non-polar solvents described above. It is important that the second polar solvent is immiscible in the non-polar solvent, and vice versa.

Although steps (i) and (ii) above can be performed more than once, the same solvent system, i.e., the biphasic mixture of the second polar solvent and second non-polar solvent, needn't be used in each iteration. In other words, different polar solvents can be used in conjunction with different non-polar solvents in each iteration of steps (i) and (ii).

In a preferred embodiment, there are two iterations of steps (i) and (ii) above, wherein the biphasic mixture of the first iteration comprises water as the second polar solvent and dichloromethane as the second non-polar solvent, and the biphasic mixture of the second iteration comprises about 9:1 ethanol/water as the second polar solvent and petroleum ether as the second non-polar solvent.

It is to be understood that the first and second polar solvents, and first and second non-polar solvents are independent of each other, such that the first polar solvent need not be the same as the second polar solvent, and the first non-polar solvent need not be the same as the second non-polar solvent.

Optionally, the extract concentrate obtained in step (ii) can be further purified to obtain one or more hypoglycemically active compounds in substantially purified form. Suitable methods of purification include, but are not limited to, recrystallization from solvents and solvent mixtures known to those skilled in the art, elution chromatography and combinations thereof. Methods of elution chromatography include, but are not limited to, preparative thin-layer chromatography, conventional silica gel chromatography, vacuum flash chromatography, high performance liquid chromatography, and combinations thereof. Each of the purification methods can be performed more than once, if necessary.

In a preferred embodiment, the extract concentrate obtained from the two iterations of steps (i) and (ii), above, is purified first using vacuum flash chromatography, and then using conventional silica gel chromatography to provide harunganin or vismin in substantially purified form.

In another embodiment of the invention, hypoglycemic extracts of Harungana or Vismia spp., preferably of *H. madagascariensis*, are prepared by heating plant parts in water, preferably at boiling or near boiling temperatures, for between about 1 minute to about 48 hours, preferably for between about 1 minute and about 2 hours, and most preferably for between about 2 minutes and about 15 minutes. The weight percentage of plant parts relative to water can range from about 1 to about 50 wt. %, preferably from about 5 to about 40 wt. %, and most preferably from about 10 to about 25 wt. %. The resulting aqueous decoction comprises one or more hypoglycemically active compounds, e.g., harunganin or vismin, and is useful as a hypoglycemic agent. In addition, the resulting decoction can be allowed to evaporate, either in vacuo or via air-drying, and the resulting residue can be used as a hypoglycemic agent. Furthermore, the resulting residue can be purified, via techniques described above, to obtain harunganin or vismin in substantially purified form.

Alternatively, harunganin or vismin can be obtained in substantially purified form using known methods (F. Delle Monache et al., *Tetrahedron* 35:2143–2149 (1979); F. Delle Monache et al., *Planta Med.* 40:340 (1980)).

5.2 Methods for Using Extracts of Harungana or Vismia Spp.

Extracts of Harungana or Vismia spp., prepared using the methods described in Section 5.1 above, have hypoglycemic activity. Due to the potent activity of the Harungana or Vismia spp. extracts of the present invention, the extracts are advantageously useful in veterinary and human medicine for therapeutic treatment of diabetes mellitus. Additionally, the extracts can be advantageously be used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these extracts of Harungana spp. Additionally, the extracts of Harungana spp. are useful as hypoglycemic agents for rare congenital metabolic glycogen storage disease associated with hyperglycemia.

Although the present inventors do not wish to be limited to any particular mechanism of action to explain the hypoglycemic activity of the Harungana or Vismia spp. extracts of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the extracts of Harungana or Vismia spp. can be used alone, or may be combined with any physiologically acceptable carrier such as water, an aqueous solution, normal saline, or other physiologically acceptable excipient. In general, the dosage would range from about 50–1000 mg/kg/day, preferably about 50–250 mg/kg/day.

Where an aqueous decoction of Harungana or Vismia spp. is prepared, a hypoglycemically effective amount of the aqueous decoction can be administered to a mammal or human as often as between 1 to about six times per day, preferably about three times per day, depending upon the concentration of harunganin or vismin in the aqueous decoction. It is within the purview of the health care provider who would administer the decoction to determine the optimal number of daily dosages.

The Harungana or Vismia spp. extracts can be administered by a number of routes, including, but not limited to: orally, injection including, but not limited to intravenously, intraperitoneally, subcutaneously, intramuscularly, etc. The preferred route of administration is oral. Additionally, the extracts of Harungana or Vismia spp. can be administered in conjunction with another hypoglycemic including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glucosidase inhibitor such as acarbose or miglatol; or a $\beta_3$-adrenoceptor agonist such as CL-316, 243, etc.

The extracts of Harungana or Vismia spp. of the present invention can be administered in an effective amount either as isolated form as described above or can be converted to pharmaceutically acceptable salts using a counter ion such as sodium, potassium, lithium, calcium, magnesium, zinc or iron.

In addition, the extracts of Harungana or Vismia spp. or pharmaceutically acceptable salts thereof can be used for research purposes, for example, to investigate the mechanism and activity of hypoglycemic agents.

5.3 Methods for Use of Harunganin and Vismin

Due to their potent activity, harunganin and vismin are advantageously useful in veterinary and human medicine for therapeutic treatment of diabetes mellitus. Additionally, harunganin and vismin can be advantageously used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these compounds. Additionally, harunganin and vismin are useful as hypoglycemic agents for rare congenital metabolic glycogen storage disease associated with hyperglycemia.

Harunganin or vismin, in substantially purified form, can be obtained using any of the methods described in Section 5.1, above. In addition, should harunganin or vismin in substantially purified form, become available by synthetic methods of preparation, the present invention is intended to encompass methods of using such compounds for the present methods and compositions for reducing blood glucose or treating diabetes.

Although the present inventors do not wish to be limited to any particular mechanism of action to explain the hypoglycemic activity of harunganin and vismin, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, harunganin and vismin can be used alone, together, or may be combined with any physiologically acceptable carrier such as water, an aqueous solution, normal saline, or other physiologically acceptable excipient. In general, the dosage would range from about 5–1000 mg/kg/day, preferably about 5–250 mg/kg/day.

Harunganin and vismin can be administered by a number of routes, including, but not limited to: orally, injection including, but not limited to intravenously, intraperitoneally, subcutaneously, intramuscularly, etc. The preferred route of administration is oral. Additionally, harunganin and vismin can be administered in conjunction with another hypoglycemic including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glucosidase inhibitor such as acarbose or miglatol; or a $\beta_3$-adrenoceptor agonist such as CL-316, 243, etc.

Harunganin and vismin can be administered in an effective amount either in their phenolic form or as pharmaceutically acceptable phenolate salts using a counter ion such as sodium, potassium, lithium, calcium, magnesium, zinc or iron.

In addition, harunganin and vismin, or pharmaceutically acceptable salts thereof, can be used for research purposes, for example, to investigate the mechanism and activity of hypoglycemic agents.

The following series of Examples are presented by way of illustration and not by way of limitation on the scope of the invention.

6. EXAMPLE: PREPARATION OF AN AQUEOUS DECOCTION FROM H. MADAGASCARIENSIS 150 g of powdered leaves or bark from *H. madagascariensis* are boiled in 1 L of water for 10 minutes. 40 mL of the resulting hypoglycemic decoction is administered to a patient orally, three times a day.

7. EXAMPLE: ISOLATION AND CHARACTERIZATION OF HARUNGANIN AND VISMIN

7.1 Materials and Methods

Analytical high performance liquid chromatography (HPLC) was performed on a Hitachi Model D-6500 Chromatography Data Station equipped with an L-6200A pump, an AS-2000 autosampler, an L-4500 A diode array detector and a Sedex 55 light scattering detector connected in parallel; and a Primesphere C18 HC, 4×50 mm (5 μm) HPLC column. All chromatographic runs were performed at ambient temperature. HPLC grade solvents were used without further purification.

Nuclear magnetic resonance (NMR) spectra were recorded on a Varian Unity Plus 400 or a Varian Unity 400 spectrometer. $^1$H NMR spectra were performed at 400 MHz; $^{13}$C NMR spectra were performed at 100 MHz. NMR spectra of compounds were recorded in deuterated acetone. One and two-dimensional NMR experiments, i.e., Distortionless Enhancement Polarization Transfer (DEPT), H—H Correlation Spectroscopy (COSY), Heteronuclear Multiple Quantum Correlation (HMQC), Heteronuclear Multiple Bond Correlation (HMBC) and long-range Heteronuclear Chemical Shift Correlation (HETCOR), provided molecular structure information. MS spectra were recorded on a Kratos MS-50 in high resolution power electron impact scanning mode, 70 ev. Resolution was set to 2000, the scanning rate was 10 sec/decay, the temperature gradient from 500° to 300° C. was increased at a rate of 50°/min. IR spectra were recorded on a Perkin-Elmer 1600 Series FTIR. UV spectra were recorded on a Perkin-Elmer Lambda 2 UV/VIS spectrometer or taken directly from the Hitachi diode-array UV detector on the HPLC system.

7.2 Isolation of Harunganin and Vismin Using Solvent Extraction

Shredded and ground whole plant material (22.2 kg) from *H. madagascariensis* was stirred in 220 L of 8:2 ethanol/water for 24 hours at room temperature. The resulting ethanol/water solution was filtered through 2.5 kg of celite, concentrated, and the resulting mixture was partitioned between dichloromethane and water. The dichloromethane phase was concentrated under reduced pressure using rotary evaporation, and the resulting residue was partitioned between petroleum ether and ethanol/water (9:1). Evaporation of the petroleum ether phase yielded 513 g of hypoglycemically active extract concentrate.

The extract concentrate was further purified using vacuum flash chromatography according to the following protocol: A 443 g portion of the extract concentrate was adsorbed onto 1 L of silica gel (J. T. Baker, Inc., Phillipsburg, N.J., 40 µm) and placed onto a 3.5 L bed of silica gel equilibrated in hexane, producing a final bed size of 22 (dia.)×27 cm. The first fraction (F1) was eluted with hexane and the second fraction (F2) was eluted with hexane/ethyl acetate (6:1). The solvent was evaporated from F2, and 162 g of a dark resin containing anthracenone compounds harunganin and vismin was obtained. A 50 g portion of the dark resin was chromatographed on a 10 (dia.)×20 cm column containing silica gel (J. T. Baker, Inc., Phillipsburg, N.J., 40 µm). A combination of 30×200 mL fractions, followed by 26×500 mL fractions, were eluted with 5:1 hexane/ethyl acetate. Fractions containing harunganin and vismin were pooled based on HPLC analysis and yielded 15.5 g of a further fraction containing approximately 30% of a mixture of harunganin and vismin. An 11.5 g portion of this further fraction was chromatographed, using a 9:1 methanol/water eluent, on a 4.8 (dia.)×25 cm column containing C-18 LC packing (Bakerbond, 40 µM) equilibrated in 9:1 methanol/water, to obtain 2.15 g (0.050%) of harunganin and 1.05 g (0.024%) of vismin.

Isolation of the anthracenone compounds harunganin and vismin is shown schematically in Scheme I, below.

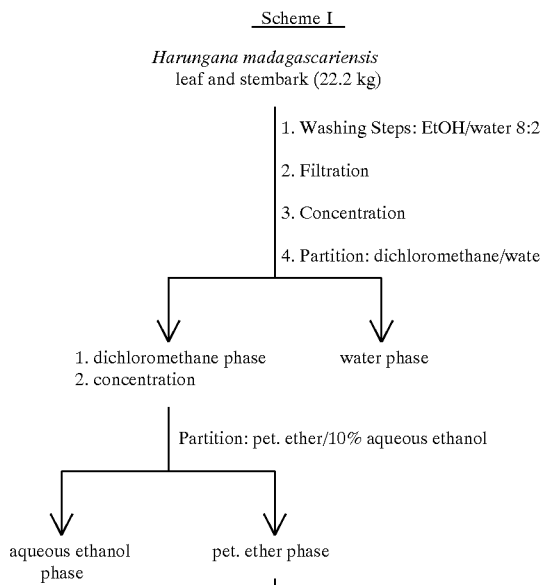

Scheme I

*Harungana madagascariensis*
leaf and stembark (22.2 kg)

1. Washing Steps: EtOH/water 8:2
2. Filtration
3. Concentration
4. Partition: dichloromethane/water 1:1 dichloromethane phase → 1. concentration
water phase

Partition: pet. ether/10% aqueous ethanol aqueous ethanol phase
pet. ether phase
1. Vacuum flash chromatography
2. Silica liquid chromatography
3. C-18 liquid chromatography harunganin (2.15g) & vismin (1.05g)

7.3 Structure Elucidation of Harunganin and Vismin

7.3.1 Spectroscopic Properties of Harunganin

Using the isolation procedure described in Section 7.2, above, harunganin was obtained as an amorphous orange solid. Its structure was identified by comparison of its spectroscopic properties with reported values (M. Nicoletti et al., *Tetrahedron* 38:3679 (1982)). Its molecular formula, $C_{30}H_{36}O_4$, was determined by HREIMS m/z 460.2616 ($M^+$, Δ0.53 ppm of calc.) and a DEPT $^{13}C$ NMR spectrum. Table 1, below, lists assigned $^{13}C$ and $^1H$ chemical shifts for harunganin.

TABLE 1

NMR Data for Harunganin

| Atom # | $^{13}C$ | $^1H$ | HMBC Correlations |
|---|---|---|---|
| 1 | 192.2 (s) | — | C-3, C-4, C-14 |
| 2 | 105.0 (d) | 5.86 (1H,s) | |
| 3 | 181.8 (s) | — | |
| 4 | 50.9 (s) | — | |
| 5 | 141.1 (s) | — | |
| 6 | 113.1 (d) | 7.50 (1H,s) | C-4, C-8, C-12, C-14 |
| 7 | 137.5 (s) | — | |
| 8 | 126.0 (s) | — | |
| 9 | 140.3 (s) | — | |
| 10 | 113.4 (d) | 6.65 (1H,s) | C-8, C-11, C-12, C-25 |
| 11 | 156.6 (s) | — | |
| 12 | 112.3 (s) | — | |
| 13 | 164.7 (s) | — | |
| 14 | 108.8 (s) | — | |
| 15/15' | 41.3 (t) | 3.02 (2H,dd,7.6,14) | C-4, C-5, C-16/16', C-17/17' |
|  |  | 2.76 (2H,dd,7.2,14)) | C-3, C-4, C-16/16', C-17/17' |
| 16/16' | 119.5 (d) | 4.70 (2H,pt,1.2,7.2) | C-18/18', C-19/19' |
| 17/17' | 134.6 (s) | — | |
| 18/18' | 25.83 (q) | 1.43 (6H,d,0.8) | C-16/16', C-17/17', C-19/19' |
| 19/19' | 18.1 (q) | 1.48 (6H,s) | C-16/16', C-17/17', C-18/18' |
| 20 | 28.0 (t) | 3.65 (2H,d 6.4) | C-7, C-9, C-21, C-22 |
| 21 | 124.5 (d) | 5.03 (1H,pt,1.2,6.4) | |
| 22 | 131.6 (s) | — | |
| 23 | 25.75 (q) | 1.67 (3H,d,1.2) | C-21, C-22, C-24 |
| 24 | 18.3 (q) | 1.93 (3H,d,0.8) | C-21, C-22, C-23 |
| 25 | 20.9 (q) | 2.41 (3H,s) | C-8, C-9, C-10 |
| OH | — | 10.08 (1H,s) | C-10, C-11 |

7.3.2 Spectroscopic Properties of Vismin

Using the isolation procedure described in Section 7.2, above, vismin was obtained as an amorphous orange solid. Its structure was identified by comparison of its spectroscopic properties with reported values (M. Nicolletti et al., *Tetrahedron* 38:3679 (1982); F.Delle Monache et al., *Planta Med.* 40:340 (1980)). Its molecular formula, $C_{25}H_{28}O_4$, was determined by HREIMS m/z 392.1991 ($M^+$, Δ0.86 ppm of calc.) and a DEPT $^{13}C$ NMR spectrum. Table 2, below, lists the assigned $^{13}C$ and $^1H$ chemical shifts for vismin.

TABLE 2

NMR Data for Vismin

| Atom # | $^{13}C$ | $^1H$ | HMBC Correlations |
|---|---|---|---|
| 1 | 192.3 (s) | — | |
| 2 | 104.9 (d) | 5,84 (1H,s) | C-3, C-4, C-14 |
| 3 | 181.8 (s) | — | |
| 4 | 50.7 (s) | — | |
| 5 | 141.8 (s) | — | |
| 6 | 116.0 (d) | 7.42 (1H,s) | C-4, C-8, C-12, C-14 |
| 7 | 139.6 (s) | — | |
| 8 | 118.7 (d) | 7.08 (1H,s) | C-6, C-10, C-12, C-20 |
| 9 | 142.6 (s) | — | |
| 10 | 112.1 (d) | 6.62 (1H,d,1.2) | C-8, C-11, C-12, C-20 |
| 11 | 158.3 (s) | — | |
| 12 | 111.8 (s) | — | |
| 13 | 164.5 (s) | — | |
| 14 | 109.2 (s) | — | |

TABLE 2-continued

NMR Data for Vismin

| Atom # | $^{13}$C | $^{1}$H | HMBC Correlations |
|---|---|---|---|
| 15/15' | 41.1 (t) | 3.30 (2H,dd,7.6,14) | C-4, C-5, C-16/16', C-17/17' |
|  |  | 2.77 (2H,dd,6.4,14) | C-3, C-4, C-16/16', C-17/17' |
| 16/16' | 119.5 (d) | 4.67 (2H,m) | C-18/18', C-19/19' |
| 17/17' | 134.7 (s) | — |  |
| 18/18' | 25.8 (q) | 1.43 (6H,s) | C-16/16', C-17/17', C-19/19' |
| 19/19' | 18.1 (q) | 1.49 (6H,s) | C-16/16', C-17/17', C-18/18' |
| 20 | 22.0 (q) | 2.40 (3H,s) | C-8, C-9, C-10 |
| OH | — | 10.02 (1H,s) | C-10 or 12, C-11 |

8. EXAMPLE: REDUCTION OF PLASMA GLUCOSE

This experiment illustrates the effectiveness of harunganin in reducing plasma glucose levels in obese diabetic db/db mice, a model recognized by those skilled in the art as being a representative model of non-insulin-dependent diabetes mellitus (NIDDM) and useful in predicting hypoglycemic activity in mammals, including humans. The results obtained using harunganin are compared with those obtained using metformin, a drug that is currently used to treat NIDDM.

8.1 Materials and Methods

Harunganin was obtained and purified as described in Section 7.2, above. Metformin (1,1-dimethylbiguanide) was purchased from Sigma Chemical Co. (St. Louis, Mo., USA; catalog No. D-5035).

Genetically altered obese diabetic mice (designated C57BL/Ks-db/db) (hereinafter "db/db" mice) were purchased from The Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and 50% relative humidity, and were maintained on a diet of Purina rodent chow and water ad libitum. Prior to treatment, blood was collected from the tail vein of each animal and assayed for plasma glucose. Mice that had plasma glucose levels between 350 and 600 mg/dl were used in the experiment. Each treatment group consisted of eight mice that were distributed so that the mean glucose levels were equivalent in each group at the start of the study.

db/db Mice received, orally by gavage, either vehicle, harunganin at 5 mg/kg (q.d., 2 days), harunganin at 50 mg/kg (single dose), or metformin (250 mg (1510 mol.)/kg (q.d., 2 days)). Compounds were delivered in a liquid vehicle containing 0.25% (w/v) carboxymethylcellulose, 1% (v/v) Tween 60, and up to 10% (v/v) dimethyl sulfoxide (DMSO) in a volume of 10 ml/kg. Blood was sampled from the tail vein three hours post-administration of compound (3 and 27 hours), and analyzed for plasma glucose levels. Individual body weights and mean food consumption (each cage) were also measured after 24 h. Plasma glucose levels were determined calorimetrically using glucose oxidase (Sigma Chemical Co.; Sigma catalog No. 315). Significant differences between groups (comparing drug-treated to vehicle-treated) were evaluated using analysis of variance and Fisher's post-hoc test. Results are presented in FIG. 1 and Tables 3 and 4 below.

8.2 Results

Oral administration of harunganin produced significant dose dependent reductions in plasma glucose in db/db mice (FIG. 1 and Table 3). Statistically significant reductions in plasma glucose levels were observed 3 hours after treatment with harunganin relative to treatment with vehicle (control). Three hours following the initial dose of harunganin, plasma glucose was reduced by 97 mg/dl in mice administered with 5 mg/kg (q.d.) (P<0.05) and approximately by 153 mg/dl in mice administered with 50 mg/kg (single dose) (P<0.05). In comparison, mice that received 250 mg (q.d.) of metformin showed only a 50 mg/dl reduction of plasma glucose after 3 hours. The anti-hyperglycemic effect of harunganin occurred in the absence of any measurable effect on food intake or body weight (Table 4), indicating that the drug, i.e., harunganin or metformin, rather than a decrease in food intake, was responsible for the reduction of plasma glucose. These data indicate that harunganin is an effective oral anti-hyperglycemic agent in a rodent model of insulin resistance, obesity and NIDDM.

TABLE 3

Effects of Compounds on Blood Glucose in Diabetic db/db Mice

| Treatment | Dose (mg/kg) | Change in Glucose (mg/dl) 3 h | P Value | Change in Glucose (mg/dl) 27 h | P Value |
|---|---|---|---|---|---|
| Vehicle | — | −5.6 | NA | −5.8 | NA |
| Metformin | 250 (q.d.) | −50.3 | 0.0556 | −171.6 | <0.0001 |
| Harunganin | 5 (q.d.) | −97 | 0.0008 | −58 | 0.0078 |
| Harunganin | 50 (single dose) | −152.6 | <0.0001 | −36 | 0.704 |

NA = non-applicable

TABLE 4

Effects of Compounds on Body Weight and Food Consumption in Diabetic db/db Mice

| Treatment | Dose (mg/kg) | Change in Body Weight (g) 24 h | Food Consumption (g/mouse) 0–24 h |
|---|---|---|---|
| Vehicle | — | −0.1 | 5.8 |
| Metformin | 250 (q.d.) | −0.2 | 4.7 |
| Harunganin | 5 (q.d.) | −0.1 | 5.7 |
| Harunganin | 50 (single dose) | 0.1 | 5.5 |

9. EXAMPLE: TIME COURSE EFFECT ON PLASMA GLUCOSE

This experiment illustrates the time course of the reduction of plasma glucose levels with harunganin treatment.

9.1 Materials and Methods

Animals and experimental conditions were the same as described for Section 8.1, above. db/db Mice received, orally by gavage, either vehicle or harunganin administered at 100 mg/kg (single dose). Blood was obtained from the tail vein prior to treatment (t=0), and at 1.5, 3, 4.5, 6 and 24 hours following the treatment, and analyzed for plasma glucose levels. Results are presented in FIG. 2.

9.2 Results

Figure 2:
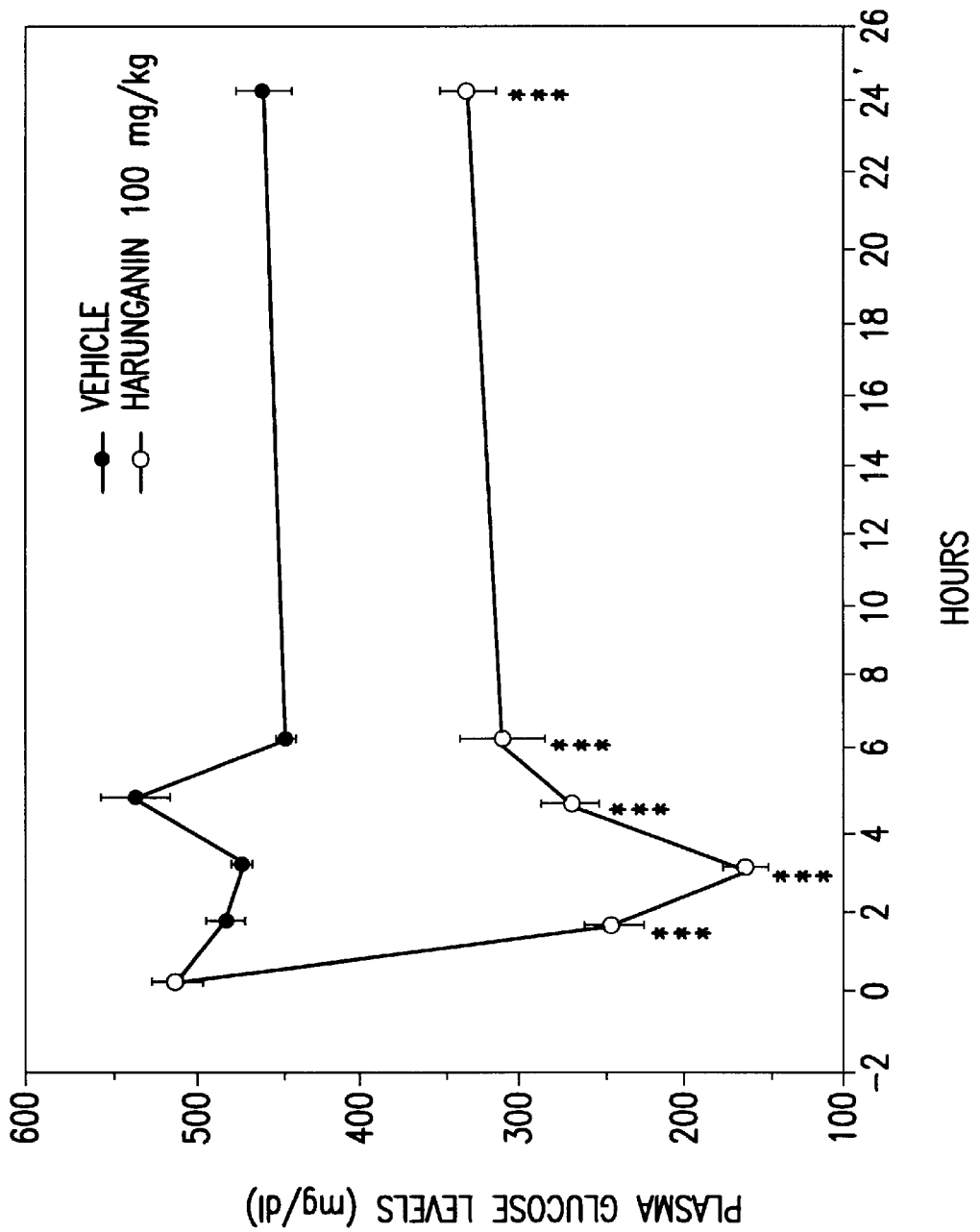

Harunganin significantly decreased plasma glucose levels as early as 1.5 hours post-administration and reached its maximum glucose lowering activity at 3 hours (FIG. 2). Plasma glucose levels rebounded between 3 and 6 hours post-administration, but the rebound slowed down substantially thereafter, and the plasma glucose levels of mice administered with harunganin remained significantly lower than those treated with the vehicle only, i.e., approximately 150 mg/dl lower, for up to 24 hours. These data indicate that harunganin significantly decreases plasma glucose levels for up to 24 hours with a 100 mg/kg single dose in the rodent model of insulin resistance, obesity and NIDDM.

10. EXAMPLE: EFFECT ON GLUCOSE DISPOSAL

This experiment illustrates the beneficial effects of harunganin on glucose disposal using an oral glucose tolerance test (hereinafter "OGTT") in db/db mice.

10.1 Materials and Methods

Animals and experimental conditions were the same as for Section 8.1, above. db/db Mice received, orally by gavage, once daily for 2 days either vehicle, harunganin administered at 5, 25 or 50 (mg/kg), or metformin (250 mg (1510 mol)/kg). Animals were fasted overnight prior to receiving the third dose of the compounds. On day three of the study, an oral glucose load (2 g/kg) was given three hours post-treatment. Blood was obtained from the tail vein prior to administration of the glucose load (t=0), and at 15, 30, 60, and 120 minutes following the glucose load, and analyzed for plasma glucose levels. Results are presented in FIGS. 3 and 4.

10.2 Results

Figure 3:
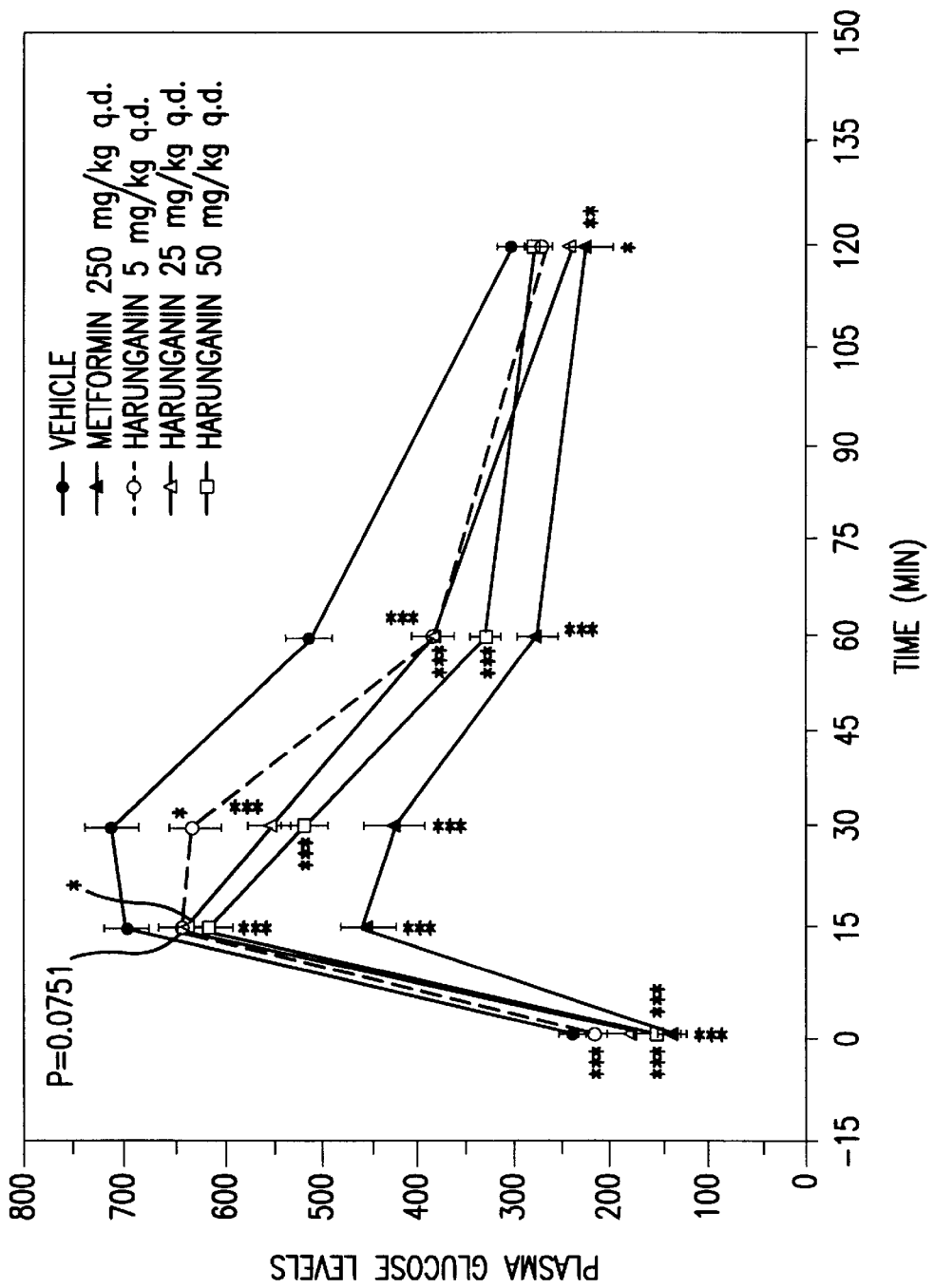
Figure 4:
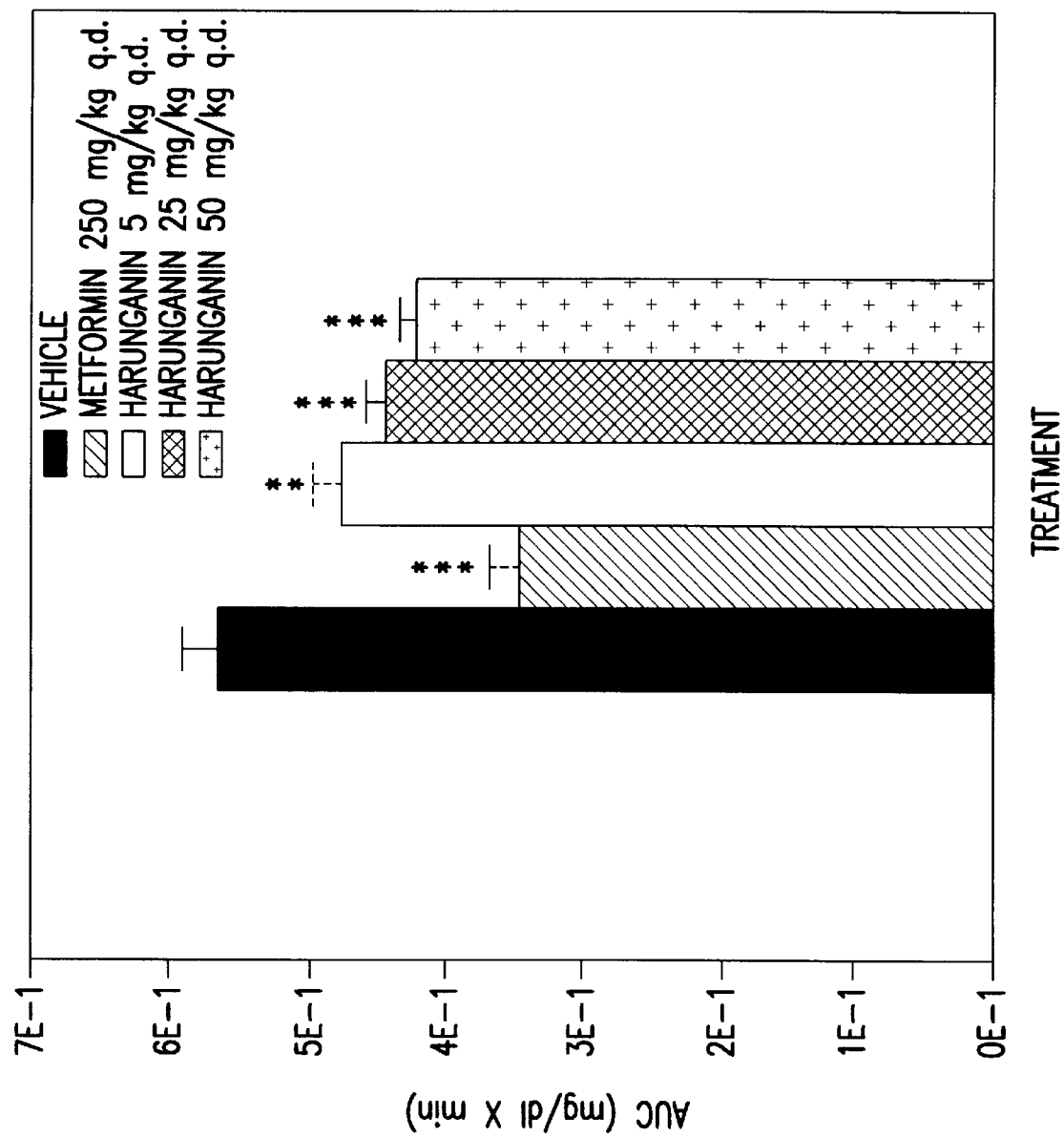

Harunganin enhanced glucose disposal (i.e., enhanced the transfer of glucose from the bloodstream to the tissues) in an OGTT using db/db mice (FIGS. 3–4). Harunganin at all doses (5, 25 and 50 mg/kg) significantly suppressed the postprandial glucose levels at all time points after the glucose load (FIG. 3). The oral glucose tolerance was significantly improved, compared to control, by administering harunganin as indicated by the area under the curve (FIG. 4; *P<0.05; P<0.01; *P<0.001). This effect was in a dose-dependent manner (FIG. 4). These data indicate that harunganin enhances glucose utilization and improves the rate of glucose disposal in a rodent model of insulin resistance, obesity, and NIDDM.

11. EXAMPLE: EFFECTS ON GLUCOSE TRANSPORT IN 3T3-L1 ADIPOCYTES

This example illustrates the ability of harunganin and vismin to directly stimulate glucose transport in 3T3-L1 adipocytes, an art recognized in vitro system that represents an important mode of action for glucose utilization and disposal in mammals, and is predictive of the hypoglycemic activity of compounds in vivo.

11.1 Materials and Methods

Murine 3T3-LI preadipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days post-confluence (day 0) according to the standard protocol of Frost and Lane (S. Frost et al., *J. Biol. Chem.* 260:2646–2652 (1985)). Following differentiation, adipocytes were maintained in DMEM containing 10% fetal bovine serum, and provided with fresh medium every 2–3 days. Adipocytes employed in this study were used on days 7–10 post-differentiation. On the day of the experiment, adipocytes were washed with phosphate-buffered saline and switched to serum-free DMEM medium.

Adipocytes were treated (in triplicate) for 18 hr with the indicated concentrations of harunganin and vismin. Concentrated stock solutions of harunganin and vismin were freshly prepared in dimethyl sulfoxide (DMSO) and diluted into culture medium. The final concentration of DMSO was 0.4% (v/v) which was also included in basal conditions. Following overnight (18 hr) treatment, the culture medium was aspirated and the monolayers washed with Krebs-Ringer Hepes buffer. To assess the effects of the compounds on basal glucose transport, 2-deoxy-D-glucose uptake (an indicator of glucose transport) was measured in the absence of insulin stimulation. To determine if 18 hr exposure to compounds harunganin and vismin potentiated the stimulatory effect of insulin, adipocytes were further treated with 0.5 nM insulin (a sub-maximal concentration) for 30 minutes at 37° C. Under these assay conditions, 0.5 nM insulin stimulates glucose transport by approximately 200–400% over basal (typically 50 nmoles 2-deoxyglucose/10 minutes/well), and 100 nM insulin (a maximally effective concentration) stimulates glucose transport by approximately 1000–1500% over basal. Glucose transport assays were initiated by the addition of 2-deoxy-D-($^3$H)glucose (0.5 $\mu$Ci/ml) 100 $\mu$M final concentrations to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity was determined by liquid scintillation counting. All data were corrected for non-specific hexose uptake determined in parallel samples treated for 5 minutes with 200 mM cytochalasin B. Results are presented in FIG. 5 and FIG. 6.

11.2 Results

Figure 5:
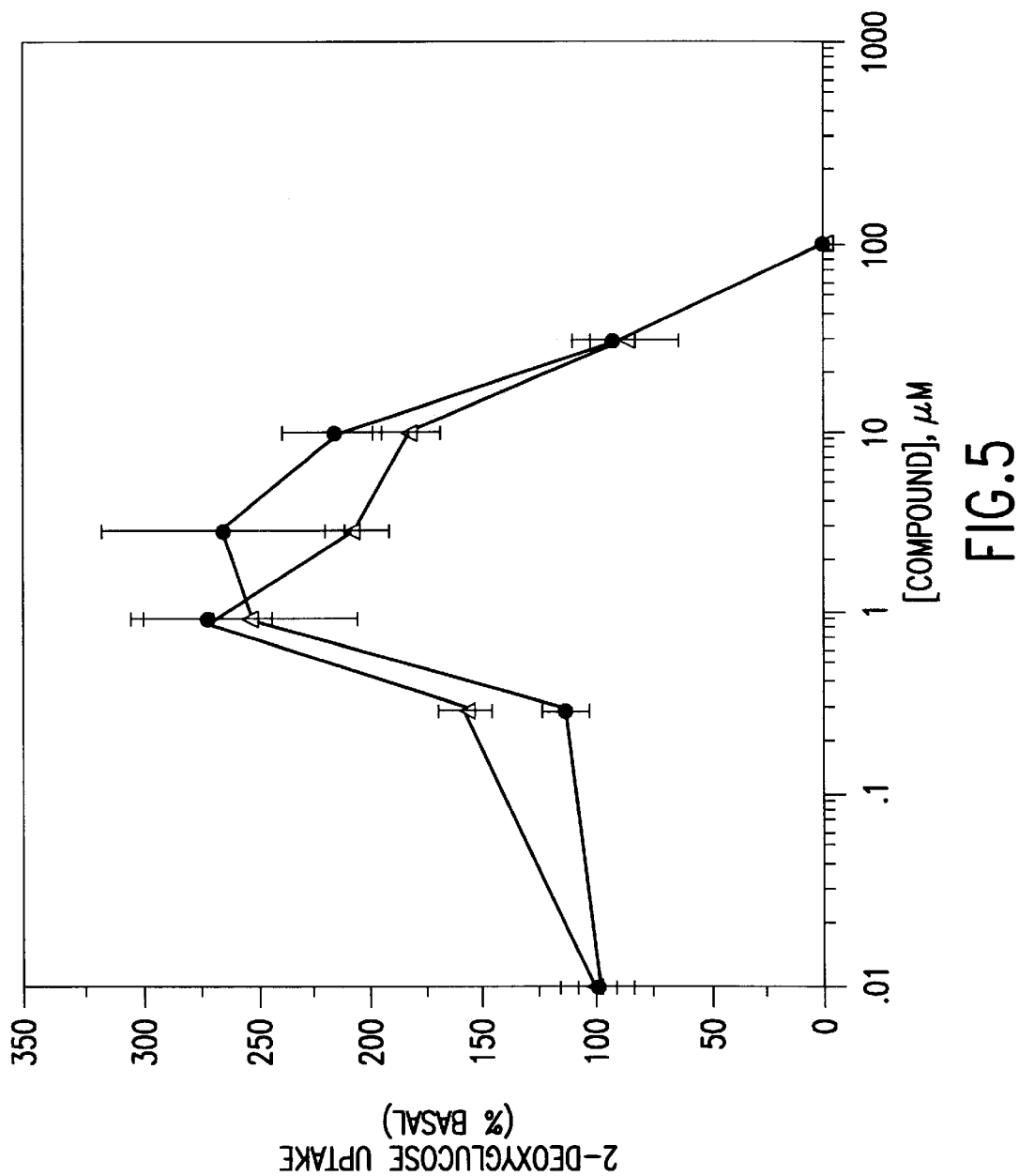
FIG. 5 is a graph showing the effects of harunganin and vismin on basal 2-deoxyglucose uptake in 3T3-L1 adipocytes: —●— for harunganin; —▲— for vismin. See Section 11.2 for details.

Harunganin increased the rate of basal glucose transport (i.e., no added insulin) in 3T3-L1 adipocytes by approximately 250%, relative to basal levels, at 1 $\mu$M and 3 $\mu$M (FIG. 5). Vismin increased the rate of basal glucose transport (i.e., no added insulin) in 3T3-L1 adipocytes by approximately 275%, relative to basal levels, at 1 $\mu$M (FIG. 5).

Figure 6:
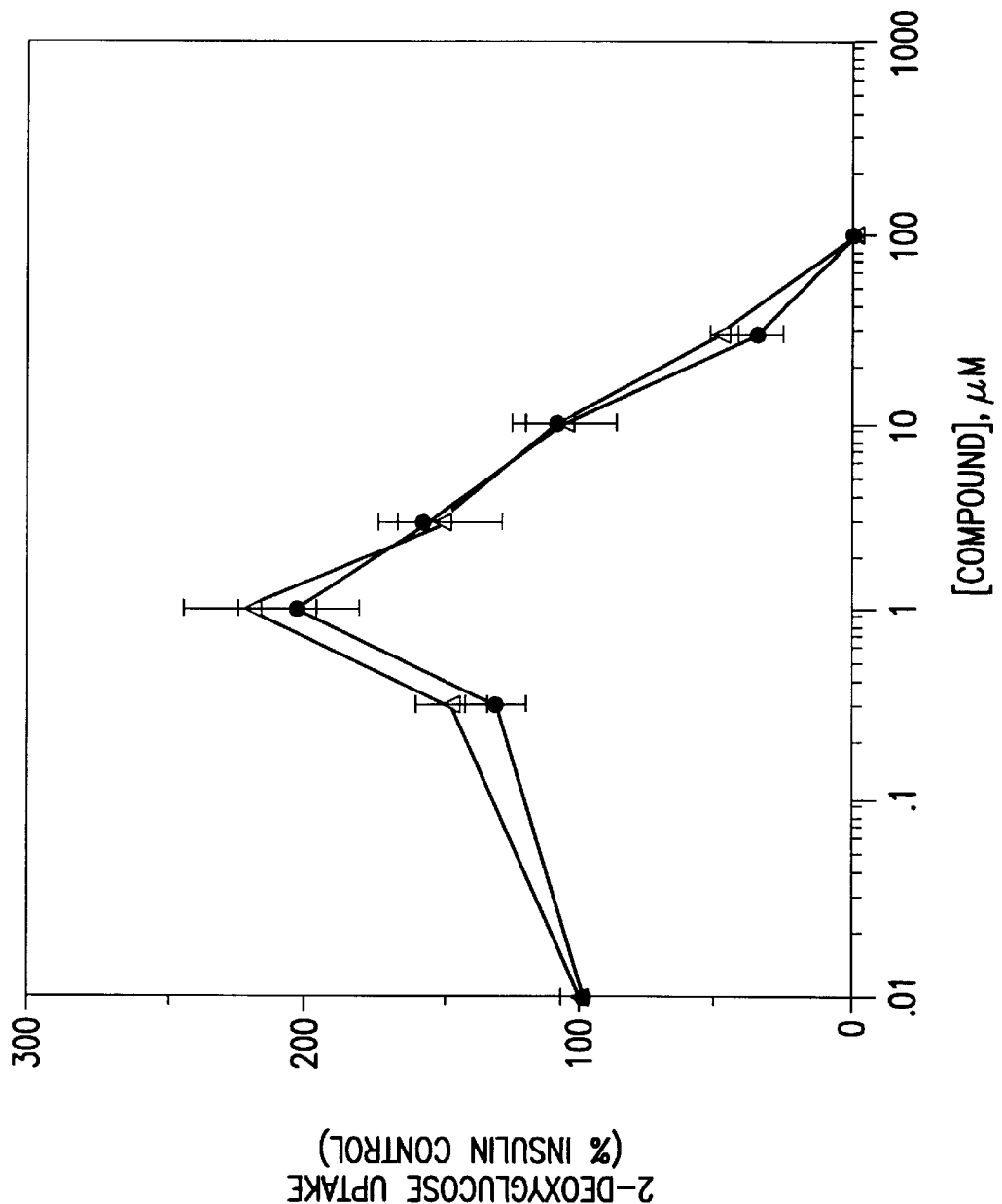
FIG. 6 is a graph showing the effects of harunganin and vismin on insulin-stimulated 2-deoxyglucose uptake in 3T3-L1 adipocytes: —●— for harunganin; —▲— for vismin. See Section 11.2 for details.

Harunganin (at 1 and 3 $\mu$M) and vismin (at 1 and 3 $\mu$M) also sensitized the glucose transport system in adipocytes to subsequent stimulation with a sub-maximal concentration of insulin (0.5 nM; FIG. 6). At 0.3, 1 and 3 $\mu$M harunganin and vismin potentiated glucose transport by approximately 60 to 100%, relative to the insulin control. (FIG. 6). As would be recognized by those skilled in the art, these data indicate that harunganin and vismin directly stimulate glucose transport in vitro, an effect that is consistent with the in vivo findings of enhanced glucose disposal and the ability to lower blood glucose.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A method for reducing the blood glucose of a mammal, comprising administering to said mammal a hypoglycemically effective amount of isolated harunganin or isolated vismin, or a pharmaceutically acceptable salt thereof, and a pharmaceutically acceptable carrier.

2. The method of claim 1, in which the pharmaceutically acceptable salt is selected from the group consisting of sodium, potassium, lithium, calcium, magnesium, zinc and iron.

3. The method according to claim 1, in which the composition is administered in conjunction with another hypoglycemic agent selected from the group consisting of a sulfonylurea, a biguanide, a thiazolidinedione, a $\beta_3$-adrenoceptor agonist, an $\alpha$-glucosidase inhibitor and insulin.

4. The method according to claim 3, in which the sulfonylurea is selected from the group consisting of acetohexamide, chlorpropamide, tolazamide, tolbutamide, glyburide, glypizide and glyclazide.

5. The method according to claim 3, in which the biguanide is metformin or buformin.

6. The method according to claim 3, in which the $\alpha$-glucosidase inhibitor is acarbose or miglatol.

7. The method according to claim 3, in which the thiazolidinedione is troglitazone.

8. A method for treatment of diabetes mellitus, comprising administering, to a mammal suffering from diabetes mellitus, a therapeutically effective amount of isolated harunganin or isolated vismin, or a pharmaceutically acceptable salt thereof, and a pharmaceutically acceptable carrier.

9. The method of claim 8, in which the pharmaceutically acceptable salt is selected from the group consisting of sodium, potassium, lithium, calcium, magnesium, zinc and iron.

10. The method according to claim 8, in which the composition is administered in conjunction with another hypoglycemic agent selected from the group consisting of a sulfonylurea, a biguanide, a thiazolidinedione, a $\beta_3$-adrenoceptor agonist, an $\alpha$-glucosidase inhibitor and insulin.

11. The method according to claim 10, in which the sulfonylurea is selected from the group consisting of acetohexamide, chlorpropamide, tolazamide, tolbutamide, glyburide, glypizide and glyclazide.

12. The method according to claim 10, in which the biguanide is metformin or buformin.

13. The method according to claim 10, in which the $\alpha$-glucosidase inhibitor is acarbose or miglatol.

14. The method according to claim 10, in which the thiazolidinedione is troglitazone.

* * * * *